US012521003B2

(12) United States Patent
Getsy

(10) Patent No.: US 12,521,003 B2
(45) Date of Patent: Jan. 13, 2026

(54) ENDOSCOPE REPROCESSOR INCLUDING ACTUATION MECHANISM FOR ACTUATING ENDOSCOPE ELEVATOR GUIDEWIRE

(71) Applicant: American Sterilizer Company, Mentor, OH (US)

(72) Inventor: Andrew Paul Getsy, Kirtland, OH (US)

(73) Assignee: American Sterilizer Company, Mentor, OH (US)

( * ) Notice: Subject to any disclaimer, the term of this patent is extended or adjusted under 35 U.S.C. 154(b) by 447 days.

(21) Appl. No.: 18/113,809

(22) Filed: Feb. 24, 2023

(65) Prior Publication Data

US 2023/0301501 A1 Sep. 28, 2023

Related U.S. Application Data

(60) Provisional application No. 63/324,282, filed on Mar. 28, 2022.

(51) Int. Cl.
*A61L 2/00* (2006.01)
*A61B 1/12* (2006.01)
*A61L 9/00* (2006.01)

(52) U.S. Cl.
CPC ........... *A61B 1/121* (2013.01); *A61L 2202/17* (2013.01); *A61L 2202/24* (2013.01)

(58) Field of Classification Search
CPC ... A61L 2/18; A61L 2/24; A61L 29/00; A61L 2202/24

(Continued)

(56) References Cited

U.S. PATENT DOCUMENTS 5,271,379 A 12/1993 Phan et al.
5,490,015 A 2/1996 Umeyama
(Continued)

FOREIGN PATENT DOCUMENTS

JP H04 314418 A 11/1992
JP 3387357 3/2003
(Continued)

OTHER PUBLICATIONS

International Search Report and Written Opinion for corresponding Application No. PCT/US2023/013792 mailed May 17, 2023.
(Continued)

*Primary Examiner* — Monzer R Chorbaji
(74) *Attorney, Agent, or Firm* — Renner, Otto, Boisselle & Sklar, LLP

(57) ABSTRACT

An endoscope reprocessor for reprocessing an endoscope. An actuation mechanism of the reprocessor includes an actuator housing and a plunger removably attachable to an elevator guidewire lever of the endoscope. A receiving chamber receives pressurized fluid from a pump to impart a pressurized fluid biasing force that displaces the plunger relative to the actuator housing in a first direction and a return actuator that imparts a return biasing force that displaces the plunger relative to the actuator housing in a second direction. A controller controls the pump to provide the pressurized fluid at a first pressure at which the pressurized fluid biasing force is greater than the return biasing force to displace the plunger lever in the first direction and a second pressure at which the return biasing force is greater than the pressurized fluid biasing force to displace the plunger and the lever in the second direction.

25 Claims, 10 Drawing Sheets

(58) Field of Classification Search
USPC ........................ 422/28, 32–33, 510, 292, 297
See application file for complete search history.

(56) References Cited

U.S. PATENT DOCUMENTS

| | | | | |
|---|---|---|---|---|
| 5,573,494 | A | 11/1996 | Yabe | |
| 5,931,833 | A | 8/1999 | Silverstein | |
| 7,341,555 | B2 | 3/2008 | Ootawara et al. | |
| 8,945,153 | B2 | 2/2015 | Surti | |
| 2007/0226927 | A1 | 10/2007 | Suzuki et al. | |
| 2014/0155696 | A1 | 6/2014 | Sakata | |
| 2016/0089125 | A1 | 3/2016 | Morimoto | |
| 2017/0258460 | A1 | 9/2017 | Zimmon | |
| 2018/0147022 | A1 | 5/2018 | Gupta | |
| 2019/0150710 | A1 | 5/2019 | Nakazato | |
| 2020/0100665 | A1 * | 4/2020 | Eibs ........................ | A61B 1/123 |
| 2020/0113426 | A1 | 4/2020 | Yoshiaki | |

FOREIGN PATENT DOCUMENTS

| | | |
|---|---|---|
| JP | 2004248800 | 9/2004 |
| JP | 2004254806 | 9/2004 |
| JP | 2009183470 | 8/2009 |
| WO | 2016103247 | 6/2016 |

OTHER PUBLICATIONS

Office Action for copending U.S. Appl. No. 18/109,563 dated Feb. 1, 2024.

* cited by examiner

ENDOSCOPE REPROCESSOR INCLUDING ACTUATION MECHANISM FOR ACTUATING ENDOSCOPE ELEVATOR GUIDEWIRE

This application claims priority to U.S. Patent Application No. 63/324,282 filed Mar. 28, 2022. This prior application is incorporated herein by reference.

FIELD OF INVENTION

This application relates generally to an endoscope reprocessor, and more particularly to an actuation mechanism for actuating an endoscope elevator guidewire and a method of reprocessing an endoscope using a reprocessor and actuation mechanism.

BACKGROUND

Endoscope reprocessors are widely used in various health care settings and are associated with a sterilization claim or a high-level disinfection claim. An example of such a reprocessor is an automated endoscope reprocessor (AER) used for reprocessing endoscopes, such as duodenoscopes, and endoscope accessories. AERs are designed to kill microorganisms in or on reusable endoscopes by exposing their outside surfaces and interior channels to a cleaning solution, for example, liquid chemical sterilant solutions or high-level disinfectant solutions.

Some endoscopes are equipped with an elevator guidewire, also referred to as an EGW, that passes through an elevator guidewire channel of the endoscope from an elevator guidewire lever in the handle at a first or proximal end of the endoscope to an elevator in a second or distal end of the endoscope. The elevator may be coupled to an endoscope accessory such as a biopsy forceps to enable manipulation of the accessory to a variety of positions. Thus, for example, forward and rearward movement of the elevator guidewire lever translates into forward and rearward movement of the elevator guidewire, which translates into raising and lowering the elevator at the distal end. The raising and lowering of the elevator, in turn, urges the biopsy forceps to various positions.

For some endoscopes the EGW channel may be open. This means that after the endoscope is used, the EGW channel must be disinfected or sterilized with a cleaning solution. There are many aspects of the design of such a channel that make this difficult. For example, the channels typically have very small inner diameters, approximately 1 mm. Also, the elevator guidewire passing through the channel typically is braided stainless steel and takes up a large portion of the volume in the channel. Since the channel is so restrictive, the flow rate of cleaning solution passing through the channel may also be low. The elevator guidewire also tends to lay or press against the inner walls of the EGW channel, which can have the effect of shadowing the channel surfaces, that is, hiding the channel surfaces from the cleaning solution. These channel characteristics are what make it challenging to efficiently disinfect or sterilize the channel with the cleaning solution.

Accordingly, there remains a need for further contributions in this area of technology.

SUMMARY OF INVENTION

The inventor found that moving an elevator guidewire within the elevator guidewire channel while cleaning solution is passing through the EGW channel aids in saturating the channel surfaces that would otherwise see reduced amounts of cleaning solution during reprocessing of an endoscope, thereby resulting in a more efficient cleaning of the channel and thus a more efficient reprocessing of the endoscope. The application relates to an endoscope reprocessor that employs an actuation mechanism that is configured to move the elevator guidewire in the EGW channel during an endoscope reprocessing cycle. According to one aspect of the invention, the actuation mechanism uses fluid pressure for example from the reprocessor's pump and a compression spring to actuate an endoscope EGW lever in two opposite directions, and thus movement of the elevator guidewire in the EGW channel in two different directions, to achieve improved cleaning of the channel. The invention realizes several advantages. For example, a reprocessor including such an actuation mechanism provides an automated means to actuate the elevator guidewire using fluid pressure from the reprocessor's cleaning solution pump, while the endoscope is being cleaned by the reprocessor. Using the working pressure of the cleaning solution self-cleans the actuation mechanism and eliminates the need for manually cleaning the EGW channel. These and other advantages are discussed throughout the detailed description.

According to one aspect of the invention, an endoscope reprocessor for reprocessing an endoscope having an elevator guidewire that passes through an elevator guidewire channel of the endoscope from an elevator guidewire lever in a handle at a first end of the endoscope to an elevator in a second end of the endoscope, includes an actuation mechanism; a basin in which the actuation mechanism and the endoscope may be arranged in fixed relation to one another; a pump that provides pressurized fluid; wherein the actuation mechanism includes an actuator housing and a plunger removably attachable to the elevator guidewire lever, wherein the actuation mechanism includes a receiving chamber to receive the pressurized fluid from the pump to impart a pressurized fluid biasing force that displaces the plunger relative to the actuator housing in a first direction and a return actuator that imparts a return biasing force that displaces the plunger relative to the actuator housing in a second direction that is opposite to the first direction; and, a controller to control the pump to provide the pressurized fluid at a first pressure at which the pressurized fluid biasing force is greater than the return biasing force to displace the plunger and the elevator guidewire lever attached thereto in the first direction and a second pressure at which the return biasing force is greater than the pressurized fluid biasing force to displace the plunger and the elevator guidewire lever attached thereto in the second direction, wherein the displacing of the plunger and the elevator guidewire lever attached thereto actuates the elevator guidewire in the elevator guidewire channel of the endoscope.

Embodiments of the invention may include one or more of the following additional features separately or in combination.

The return actuator may include a return spring, and the return biasing force may include a spring biasing force.

The actuation mechanism may include a connection port to connect the receiving chamber to a conduit of the pump to receive the pressurized fluid from the pump.

The endoscope reprocessor may further include a quick turn fitting to connect the conduit to the connection port of the actuation mechanism.

The actuator housing may include a piston cylinder, and the plunger may include a piston and a rod extending axially from the piston, wherein the piston cylinder slidably axially receives the piston therein.

The piston cylinder may have a piston side on one side of the piston and a rod side on the opposite side of the piston, and the rod side may be the side where the rod extends from the piston, and the piston side may form the receiving chamber of the actuation mechanism.

The actuation mechanism may include a rod housing fixed axially to an end of the piston cylinder, and the rod may extend axially from the piston to beyond an end wall of the rod housing through an opening in the end wall.

A portion of the rod extending beyond the end wall of the rod housing may include a lever loop attached thereto, and the lever loop may be removably attachable to the elevator guidewire lever.

The return spring may include a compression spring that circumscribes the rod and includes one end constrained by the piston and an opposite end constrained by the end wall of the rod housing.

The compression spring may be configured to be compressed at least partially in the rod housing as the plunger is displaced in the first direction.

The piston cylinder may have a piston side on one side of the piston and a rod side on the opposite side of the piston, and the rod side may be the side where the rod extends from the piston, and the rod side may be in fluid communication with the interior of the rod housing.

The rod housing may have at least one aperture therein configured to enable cleaning solution to pass therethrough to the interior of the rod housing and the rod side of the piston cylinder.

The actuator housing may be removably mountable to the endoscope.

The actuation mechanism may further include a mounting saddle configured to mount the actuator housing to the handle of the endoscope.

The mounting saddle may be made of a flexible plastic.

The mounting saddle may include first and second arms being configured to abut opposite sides of the handle, each of the first and second arms being configured with a zip tie passage to accommodate a zip tie, and the actuation mechanism may include a zip tie configured to extend through the zip tie passages and wrap around a portion of the actuator housing and a portion of the handle such that, when tightened, the zip tie mounts the actuator housing to the handle.

The actuation mechanism may include a clamp configured, when tightened, to secure the actuator housing in a fixed position relative to the clamp, and the clamp may be configured with a zip tie passage to accommodate a zip tie, and the actuation mechanism may include a zip tie configured to extend through the zip tie passage and wrap around a portion of the actuator housing and a portion of the handle such that, when tightened, the zip tie mounts the actuator housing to the handle.

The clamp may be configured to slidably receive the actuator housing axially forwards and/or rearwards and configured, when tightened, to secure the actuator housing in a fixed axial position relative to the clamp.

The actuation mechanism may include a thumb screw for tightening the clamp to the actuator housing.

The actuation mechanism may include a mounting saddle configured to mount the actuator housing to the handle of the endoscope, and the clamp and the mounting saddle may be connected together and the clamp, when tightened, may secure the actuator housing in a fixed position relative to the mounting saddle.

The actuation mechanism may be sized to be removably insertable in the basin, and the reprocessor may include a lid configured to seal the basin with the actuation mechanism and endoscope therein from the exterior of the reprocessor.

According to another aspect of the invention, a method of reprocessing an endoscope is provided, where the endoscope has an elevator guidewire that passes through an elevator guidewire channel of the endoscope from an elevator guidewire lever in a handle at a first end of the endoscope to an elevator in a second end of the endoscope, and the method includes arranging an actuation mechanism and the endoscope in fixed relation to one another in a basin of the reprocessor; mounting an actuator housing of the actuation mechanism to the endoscope and attaching a plunger of the actuation mechanism to the elevator guidewire lever, wherein the actuation mechanism includes a receiving chamber to receive pressurized fluid from a pump of the reprocessor to impart a pressurized fluid biasing force that displaces the plunger relative to the actuator housing in a first direction and a return actuator that imparts a return biasing force that displaces the plunger relative to the actuator housing in a second direction that is opposite to the first direction; and controlling the pump to provide the pressurized fluid at a first pressure at which the pressurized fluid biasing force is greater than the return biasing force to displace the plunger and the elevator guidewire lever attached thereto in the first direction and a second pressure at which the return biasing force is greater than the pressurized fluid biasing force to displace the plunger and the elevator guidewire lever attached thereto in the second direction, wherein the displacing of the plunger and the elevator guidewire lever attached thereto actuates the elevator guidewire in the elevator guidewire channel of the endoscope.

The method may include, where the return actuator includes a return spring, and the return biasing force includes a spring biasing force, controlling the pump to provide the pressurized fluid at the second pressure at which the spring biasing force is greater than the pressurized fluid biasing force to displace the plunger and the elevator guidewire lever attached thereto in the second direction.

Controlling the pump may include repeatedly displacing the plunger and the elevator guidewire lever attached thereto in the first and second directions.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

DETAILED DESCRIPTION

Figure 1:
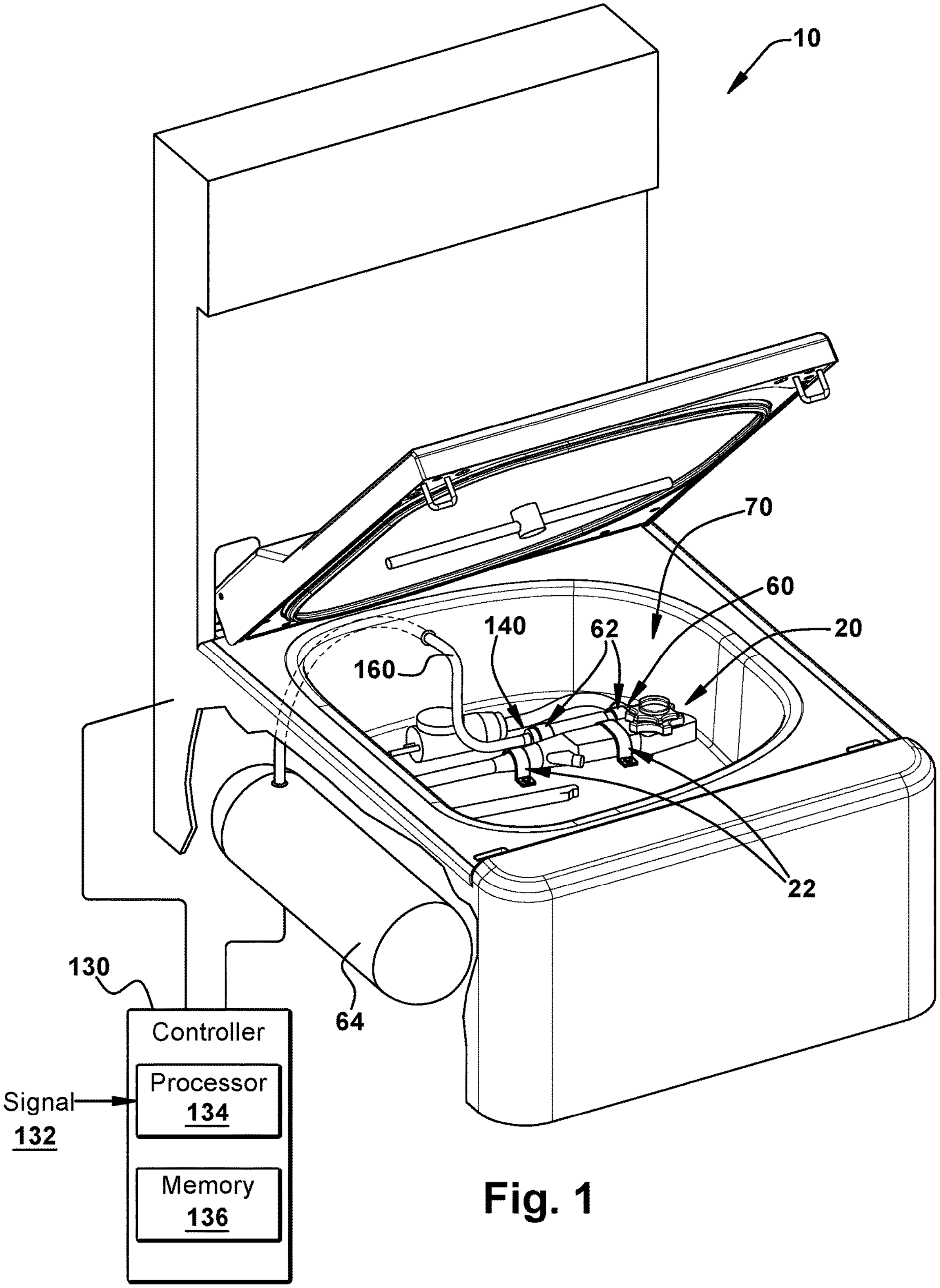
FIG. 1 is a perspective view of an endoscope reprocessor according to an embodiment of the invention, showing a lid thereof in an open position, a pump thereof in cutaway view, and a conduit thereof for connection to an actuation mechanism.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

Figure 2:
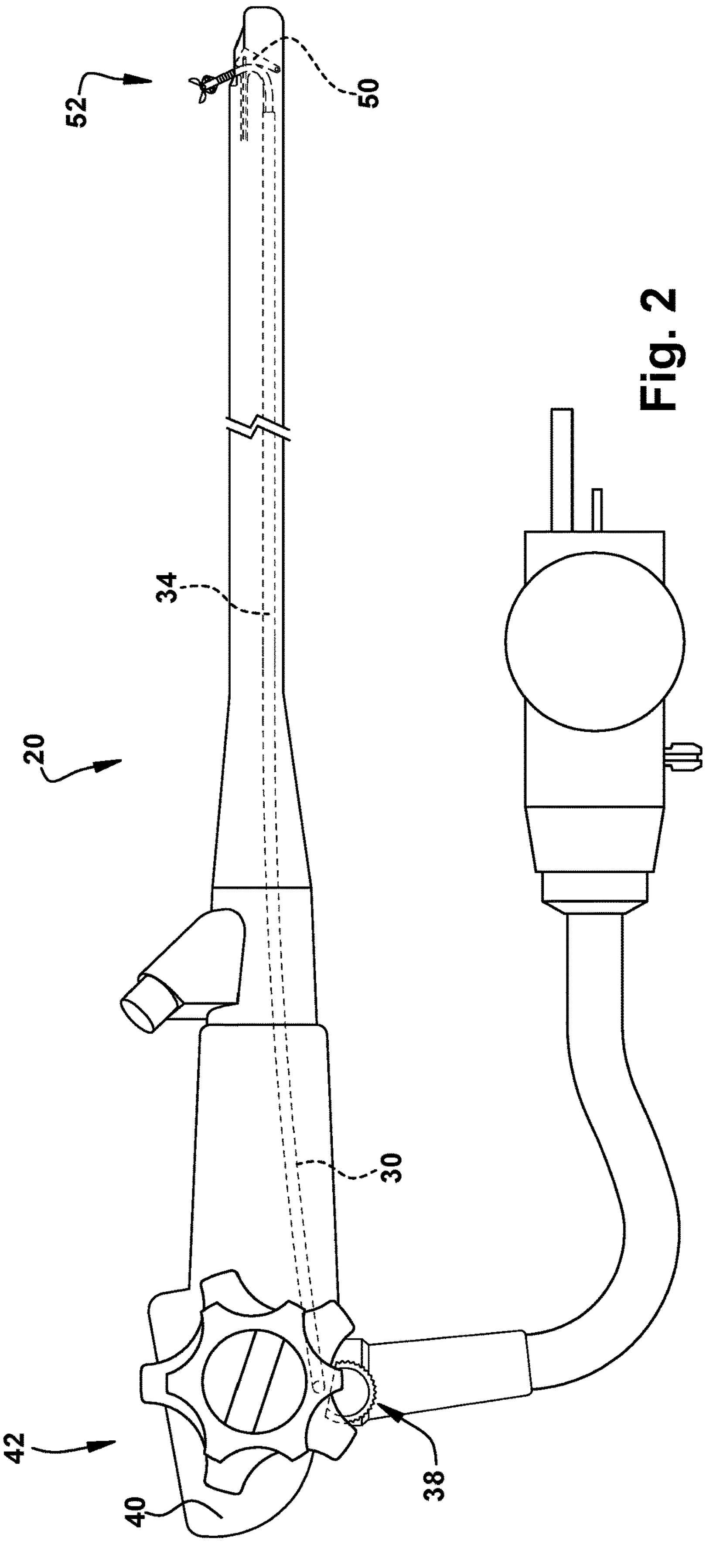
FIG. 2 is a side elevational view of an endoscope equipped with an elevator guidewire that passes through an elevator guidewire channel of the endoscope from an elevator guidewire lever in the handle of the endoscope to an elevator in the distal end of the endoscope.
Figure 3:
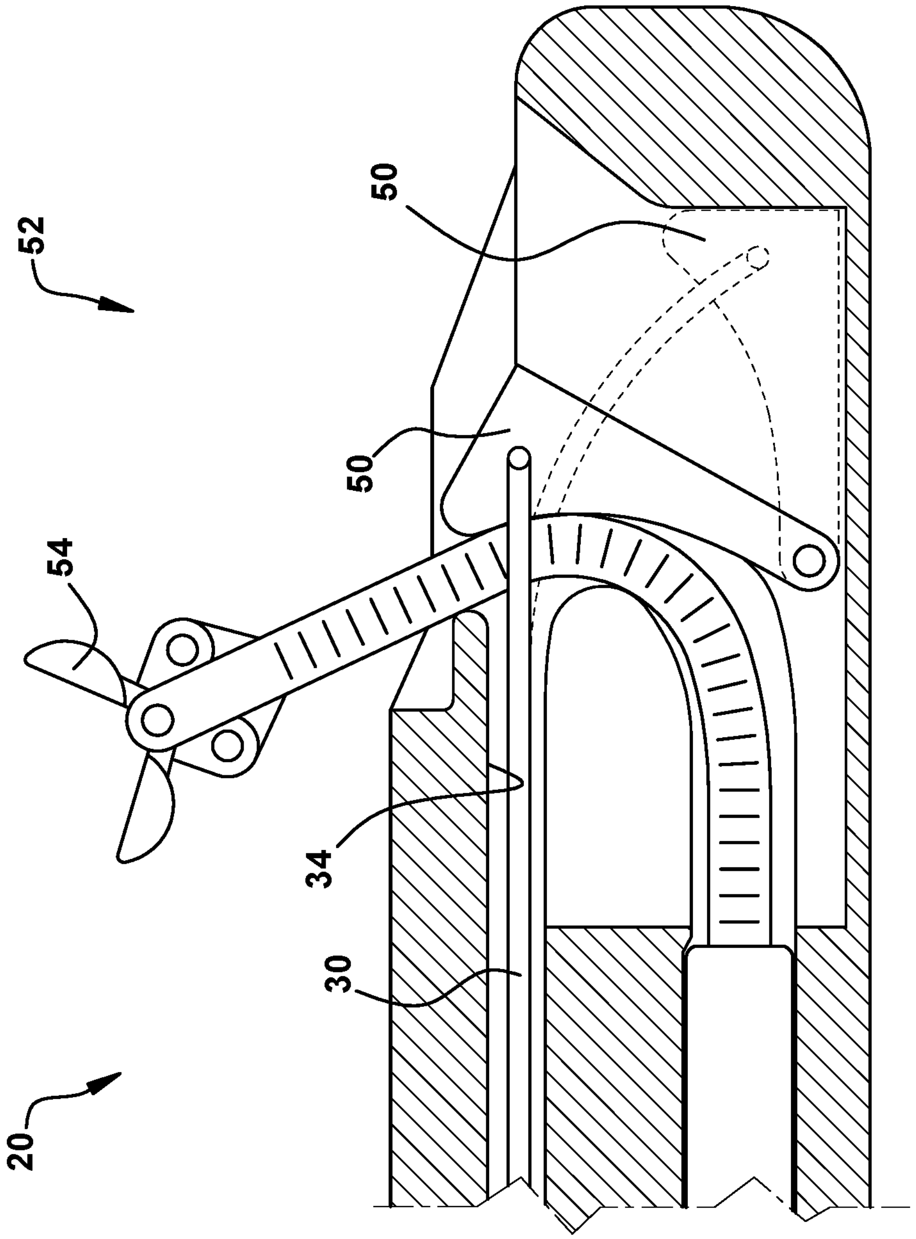
FIG. 3 is an enlarged view of the elevator of the FIG. 2 endoscope.

FIGS. 1 and 4-9 show an endoscope reprocessor 10 in accordance with an embodiment of the invention. The endoscope reprocessor 10 may be any type of system for decontaminating endoscopes, such as the endoscope 20 shown in FIGS. 2 and 3. The endoscope 20 shown in FIGS. 2 and 3 has an elevator guidewire 30 that passes through an elevator guidewire channel 34 of the endoscope 20 from an elevator guidewire lever 38 in a handle 40 at a first or proximal end 42 of the endoscope 20 to an elevator 50 in a second or distal end 52 of the endoscope 20. The elevator 50 may be coupled to an endoscope accessory such as a biopsy forceps 54 to enable manipulation of the accessory to a variety of positions. Thus, for example, forward and rearward movement of the elevator guidewire lever 38 translates into forward and rearward movement of the elevator guidewire 30, which translates into raising and lowering the elevator 50 at the second or distal end 52 of the endoscope 20. The raising and lowering of the elevator 50, in turn, urges the biopsy forceps 54 to various positions.

The endoscope reprocessor 10 includes an actuation mechanism 60, a basin 70 in which the actuation mechanism 60 and the endoscope 20 may be arranged in fixed relation to one another, and a pump 64 that provides pressurized fluid. The actuation mechanism 60 is configured to actuate the elevator guidewire 30 in the elevator guidewire channel 34 to aid in cleaning the elevator guidewire channel 34 during a reprocessing cycle of the endoscope reprocessor 10.

Figure 5:
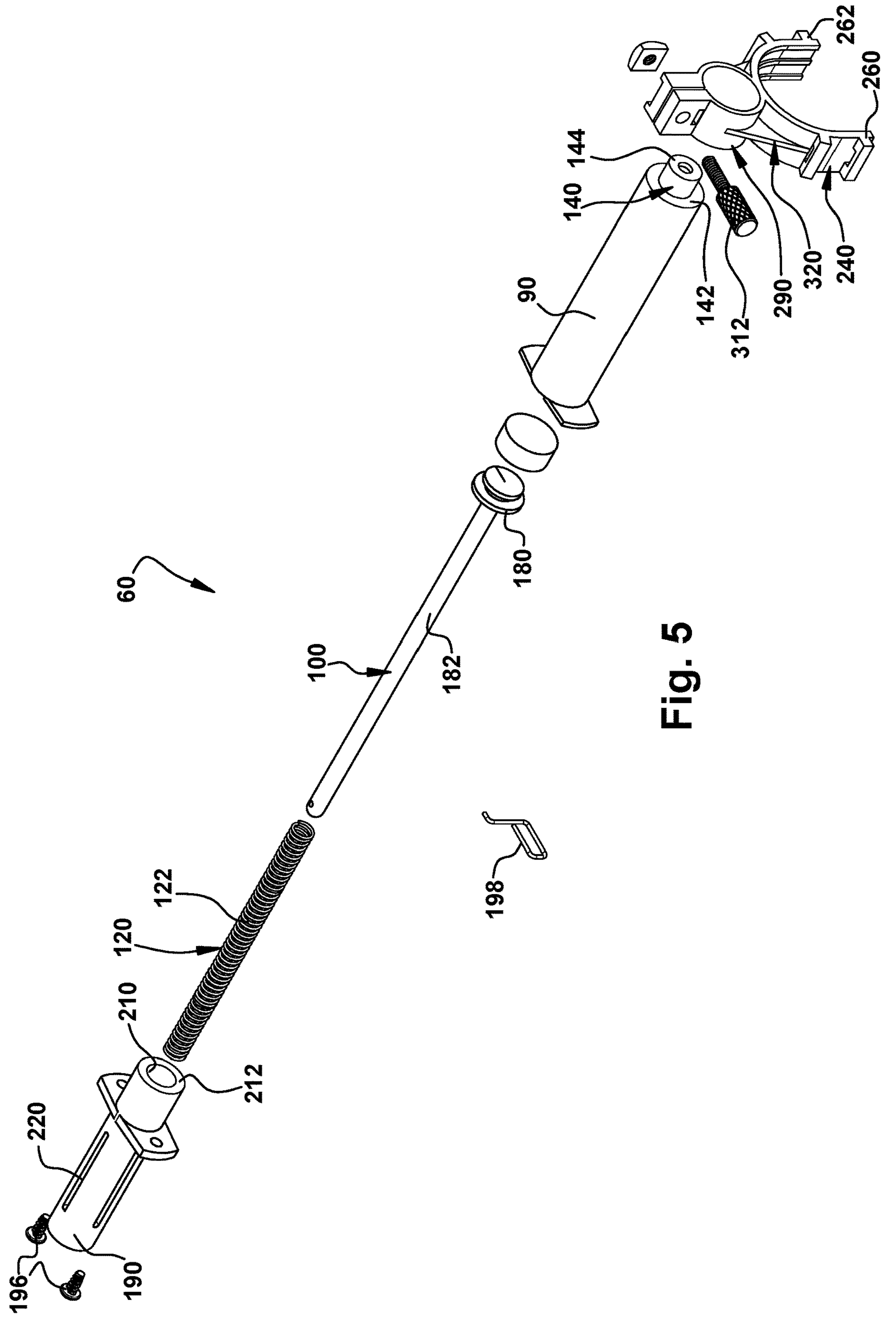
FIG. 5 is an exploded view of the FIG. 4 actuation mechanism.
Figure 6:
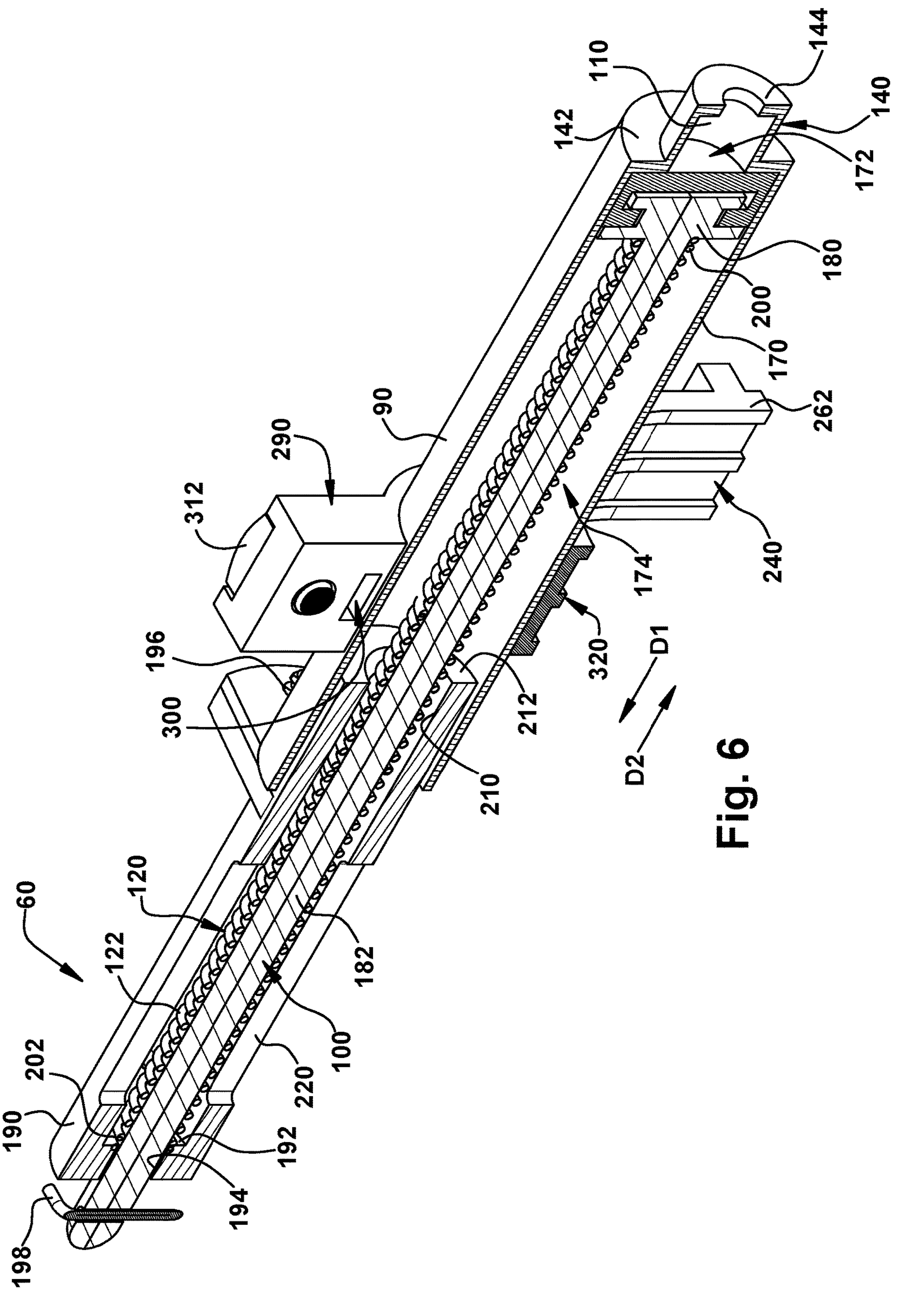
FIG. 6 is a cross sectional view of the FIG. 4 actuation mechanism.
Figure 8:
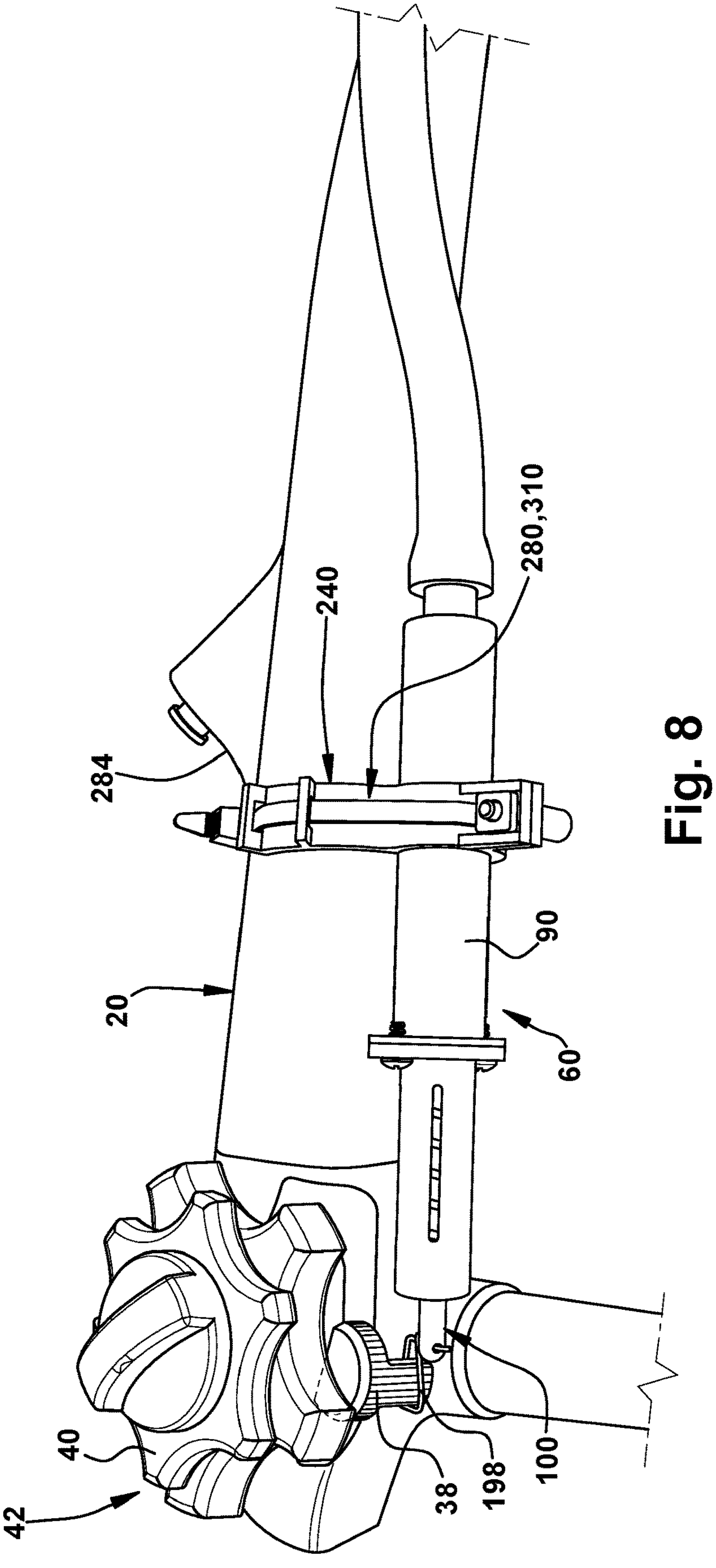
FIG. 8 is a side elevational view of the FIG. 4 actuation mechanism mounted to the FIG. 2 endoscope, showing the plunger of the actuation mechanism, and the elevator guidewire lever to which the plunger is attached, in a retracted position.
Figure 9:
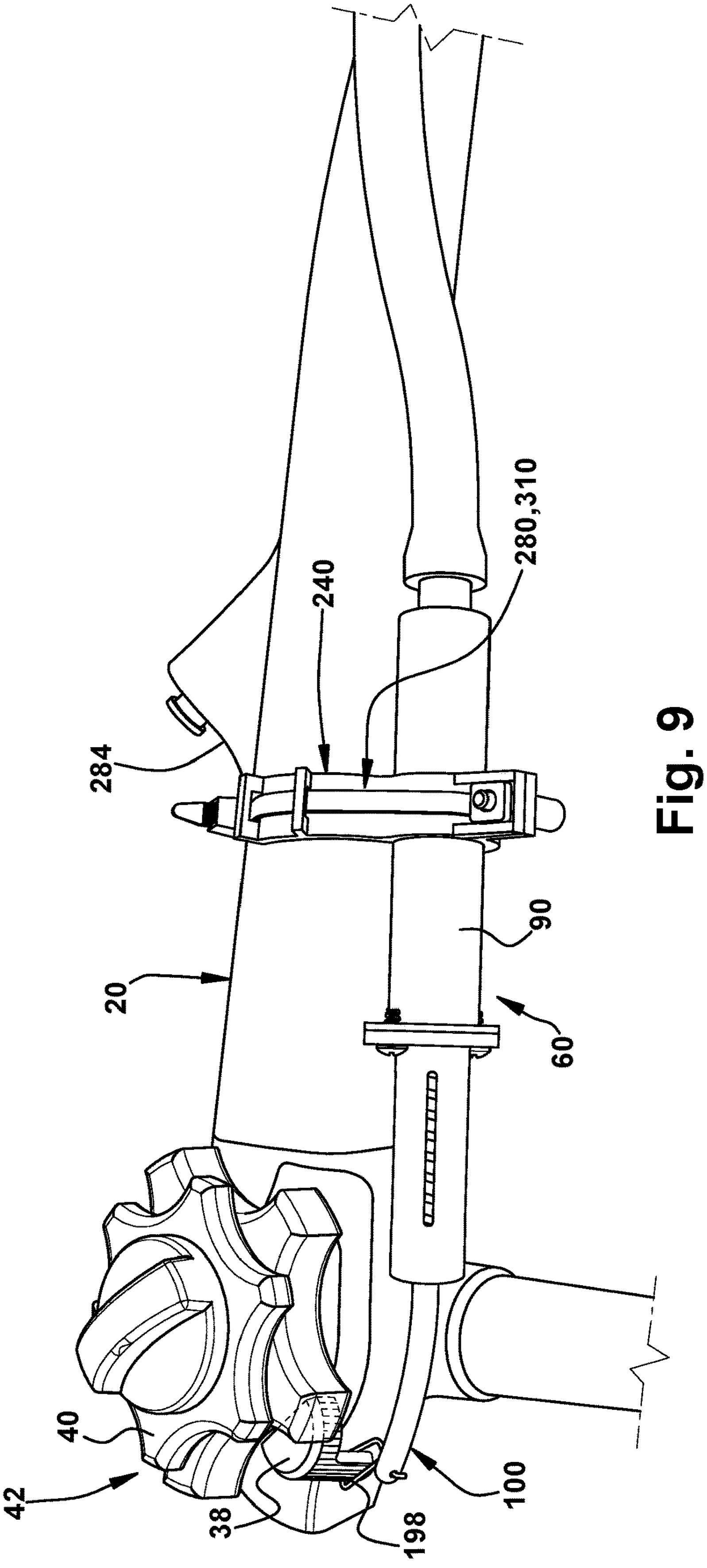
FIG. 9 is a side elevational view of the FIG. 4 actuation mechanism mounted to the FIG. 2 endoscope, showing the plunger of the actuation mechanism, and the elevator guidewire lever to which the plunger is attached, in an extended position.

As shown in FIGS. 5 and 6, the actuation mechanism 60 includes an actuator housing 90 and a plunger 100 removably attachable to the elevator guidewire lever 38 of the endoscope 20. The actuation mechanism 60 also includes a receiving chamber 110 to receive the pressurized fluid from the pump 64 of the endoscope reprocessor 10 to impart a pressurized fluid biasing force that displaces the plunger 100 relative to the actuator housing 90 in a first direction D1 and a return actuator 120 that imparts a biasing force that displaces the plunger 100 relative to the actuator housing 90 in a second direction D2 that is opposite to the first direction D1. Referring to FIGS. 1, 8 and 9, a controller 130 controls the pump 64 to provide the pressurized fluid at a first pressure at which the pressurized fluid biasing force is greater than the return biasing force to displace the plunger 100 and the elevator guidewire lever 38 attached thereto in the first direction D1 and a second pressure at which the return biasing force is greater than the pressurized fluid biasing force to displace the plunger 100 and the elevator guidewire lever 38 attached thereto in the second direction D2.

As will be described in greater detail below, the actuation mechanism 60 displaces the plunger 100 and the elevator guidewire lever 38 attached thereto thereby to actuate the elevator guidewire 30 in the elevator guidewire channel 34 of the endoscope 20, which advantageously aids in saturating channel surfaces that would otherwise see reduced amounts of cleaning solution during reprocessing of the endoscope 20. Advantageously, this results in a more efficient cleaning of the elevator guidewire channel 34 and thus a more efficient reprocessing of the endoscope 20.

Turning initially then to FIG. 1, the endoscope reprocessor 10 is shown in perspective view with the lid 80 in an open position. The actuation mechanism 60 is sized to be removably insertable in the basin 70. The lid 80 is configured to seal the basin 70, with the actuation mechanism 60 and endoscope 20 therein, from the exterior of the reprocessor 10. As shown in FIG. 1, the basin 70 is sized such that the endoscope 20 and the actuation mechanism 60 can be arranged within the walls of the basin 70.

The actuation mechanism 60 may be fixed relative to the endoscope 20 by any suitable means. In one embodiment, the actuation mechanism 60 and endoscope 20 may be clamped, fastened, bracketed, strapped, or otherwise connected to one or more walls of the basin 70, whether a side wall and/or bottom wall. In FIG. 1, for example, a first set of straps 22 fixes the endoscope 20 to the bottom wall of the basin 70 and a second set of straps 62 fixes the actuation mechanism 60 to the bottom wall of the basin 70, thereby fixing the actuation mechanism 60 relative to the endoscope 20. The straps 22, 62 may be zip ties, for example. In another embodiment, which will be described in greater detail below, the actuation mechanism 60 is fixed relative to the endoscope 20 by means of a mounting saddle. Other embodiments are contemplated, for example, dedicated cavities may be provided in the basin 70 that are contoured to receive and secure the respective endoscope and actuation mechanism therein to fix the actuation mechanism 60 relative to the endoscope 20.

The controller 130 is configured to control the reprocessing cycle of the endoscope reprocessor 10 including but not limited to the decontamination of the external and internal portions of the endoscope 20, in addition to the pump 64 to actuate the actuation mechanism 60. The decontamination may be for example by a sterilization process or a disinfection process. The controller 130 controls the pump 64 to provide fluid at the first pressure and second pressure as necessary or desired to displace the plunger 100 and the elevator guidewire lever 38 attached thereto in the respective first and second directions D1, D2. The pump 64 may be the main pump of the reprocessor 10 or a dedicated auxiliary pump. In one form, the pump 64 is an auxiliary pump that is also used to supply water pressure to the endoscope lumens during a reprocessing cycle.

The controller 130 may receive a reprocessing cycle signal 132 from a user or operator of the endoscope reprocessor 10. For example, the reprocessing cycle signal 132 may be received by a processor 134 in the controller 130. The processor 134 may include any suitable microprocessor, control processing unit (CPU), control circuitry, or the like. A memory 136 may also be provided as part of the controller 130. The memory 136 may contain stored data pertaining to operation of the reprocessor 10 that is used by the processor 134 in providing instructions to the controller 130. For example, the memory 136 may be configured to store data or a look-up table pertaining to a particular endoscope and the cycle parameters of a reprocessing cycle for the endoscope, including for example the first and second pressures at which the pump 64 is to operate.

Turning now to FIGS. 1 and 4-9, the actuation mechanism 60 includes a connection port 140 to connect the receiving chamber 110 thereof to a conduit 160 of the pump 64 to receive the pressurized fluid from the pump 64. In the illustrated embodiment, the connection port 140 is connected to an end wall 142 of the actuator housing 90. A suitable fitting or coupling, for example a quick turn fitting 144, such as a luer lock, may connect the conduit 160 to the connection port 140 of the actuation mechanism 60. The quick turn fitting 144 may aid in removably coupling the actuation mechanism 60 to the conduit 160 of the reprocessor 10 in a more efficient manner. When the conduit 160 is connected to the connection port 140, the resulting connection creates a seal to contain the pressurized fluid provided by the pump 64 and communicated to the actuation mechanism 60 by the conduit 160, connection port 140, and receiving chamber 110. Other types of connectors and/or seals may be used and are contemplated.

FIGS. 5 and 6 show greater detail of the internal components of the actuation mechanism 60. The actuator housing 90 of the actuation mechanism 60 includes a piston cylinder 170 which aids in guiding displacement of the plunger 100. The illustrated plunger 100 is made up of a piston 180 and a rod 182 that extends axially from the piston 180. The piston 180 and the rod 182 are circular shape in axial cross section and the piston 180 has a larger diameter than that of the rod 182. In the illustrated embodiment, the piston 180 has a diameter that is about two times that of the rod 182. The piston cylinder 170 has a slightly larger diameter in axial cross section than that of the piston 180. The piston cylinder 170 slidably axially receives the piston 180 therein. This sliding engagement aids in the smooth displacement of the piston 180, and thus the plunger 100 of which the piston 180 is a part, in the afore mentioned first and second directions D1, D2.

As is apparent from FIG. 6, the piston cylinder 170 defines, in part, the receiving chamber 110 of the actuation mechanism 60 that receives the pressurized fluid from the pump 64. The piston cylinder 170 has a piston side 172 on one side of the piston 180 and a rod side 174 on the opposite side of the piston 180. The rod side 174 of the piston cylinder 170 is the side where the rod 182 extends from the piston 180. The piston side 172 of the piston cylinder 170 is the side that forms the receiving chamber 110 of the actuation mechanism 60. The connection port 140 is located on the piston side 172 so that when pressurized fluid is introduced into the receiving chamber 110 through the connection port 140, and thus to the piston side 172 of the piston cylinder 170, the piston 180 is displaced accordingly. As will be appreciated, as the pump 64 provides pressurized fluid into the piston side 172 at the first pressure, the piston 180 slides within the piston cylinder 170 to displace the plunger 100 and thus the elevator guidewire lever 38 of the endoscope 20 in the first direction D1, thereby actuating the elevator guidewire 30 and the elevator 50 at the distal end 52 of the endoscope 20.

A rod housing 190 is fixed axially to an end of the piston cylinder 170 opposite the connection port 140 by, for example, a pair of fasteners 196. A portion of the rod 182 of the plunger 100 extends beyond an end wall 192 of the rod housing 190 and through an opening 194 in the end wall 192. The opening 194 is circular shape in axial cross section and has a slightly larger diameter than that of the rod 182. The end wall 192 via the opening 194 slidably axially receives the rod 182 therethrough and, by this sliding engagement, guides the rod 182 as the piston 180 is displaced within the piston cylinder 170. The portion of the rod 182 extending beyond the end wall 192 includes a lever loop 198 attached thereto. The lever loop 198 is removably attachable to the elevator guidewire lever 38 of the endoscope 20. The lever loop 198 may be made of metal wire. The rod 182 may be made of flexible plastic to enable flexure in the distal end of the rod 182 as the actuation mechanism 60 moves the rod 182 in the first and second directions D1, D2, for example, as shown in FIG. 8 where the distal end of the rod 182 is unflexed and FIG. 9 where the distal end of the rod is flexed.

The return actuator 120 as earlier described exerts the return biasing force on the plunger 100 which opposes the pressurized fluid biasing force exerted by the pressurized fluid on the plunger 100. In the illustrated embodiment, the return actuator 120 includes a return spring 122 and the return biasing force includes a spring biasing force, although it will be appreciated that other embodiments are contemplated. Thus, for example, the return actuator 120 may include a return receiving chamber for example on the rod side 174 of the piston 180 that receives pressurized fluid from the pump 64 in a like manner as the receiving chamber 110 receives on the piston side 172 of the piston 180. The piston cylinder 170 may include a fluid pressure connection port to receive the pressurized fluid in the rod side 174 of the piston cylinder 170, i.e., opposite the connection port 140 end of the piston cylinder 170, to realize a double acting piston-cylinder. In such a double acting piston-cylinder, an exhaust valve may be provided that diverts the pressurized fluid from the piston side 172 of the piston cylinder 170 to the rod side 174 of the piston cylinder 170, and vice versa to control displacement of the piston 180 in the first and second directions D1, D2.

As will be appreciated, the pressurized fluid may be water and/or cleaning solution to take advantage of the existing endoscope processor features. In another embodiment, air may be used to actuate the piston 180 instead of water or the cleaning solution.

The rod housing 190 is configured to house the reciprocating rod 182 of the plunger 100 and to receive the return spring 122 of the return actuator 120 as the return spring 122 is compressed by the piston 180 of the plunger 100. The return actuator 120 returns the piston 180, and thus the plunger 100 of which the piston 180 is a part, in the second direction D2, for example, to the end wall 142 of the actuator housing 90. In the illustrative embodiment in which the return actuator 120 includes the return spring 122, the return spring 122 may be a compression spring 122. As will be appreciated, the return spring 122 may instead be a tension spring, in which case, for example, the tension spring may be connected at its opposite ends to the piston 180 and the end wall 142 of the actuator housing 90. In other embodiments, the return spring 122 may include both a compression spring and a tension spring, for example acting on opposite sides of the piston 180.

As shown in FIG. 6, the return spring 122 circumscribes the rod 182 of the plunger 100. In this way, the rod 182 may aid in preventing buckling of the return spring 122 as the return spring 122 flexes. The return spring 122 includes an end 200 constrained by the piston 180 and an opposite end 202 constrained by the end wall 192 of the rod housing 190. In this way, the return spring 122 biases the piston 180 and plunger 100 in the second direction D2, i.e., against the biasing force imparted by the pressurized fluid on the opposite side of the piston 180. The return spring 122 is configured to be compressed at least partially in the rod housing 190 as the plunger 100 is displaced in the first direction D1 by the pressurized fluid force being greater than the spring biasing force. As the plunger 100 is displaced in the second direction D2 by the spring biasing force being greater than the pressurized fluid force, the return spring 122 unflexes to reside partially in the rod housing 190 and partially in the rod side 174 of the piston cylinder 170.

The rod 182 and return spring 122 pass through a bore 210 in the rod housing 190. The bore 210 has a slightly larger diameter than the outer diameter of the return spring 122. In this way, the bore 210 may aid in preventing buckling of the return spring 122, for example, as the return spring 122 is compressed into the rod housing 190. The inner diameter of the return spring 122 is slightly larger than the diameter of the rod 182. This too aids in preventing buckling of the return spring 122 during compression.

In the illustrated embodiment, the return spring 122 is sandwiched between the piston 180 and the end wall 192 of the rod housing 190. It will be appreciated that the return spring 122 may be integrated into the actuation mechanism 60 in additional or alternate ways. For example, the return spring 122 may be sandwiched between the piston 180 and the structure or wall 212 that surrounds the bore 210 of the rod housing 190.

As shown in FIG. 6, the rod side 174 of the piston cylinder 170 is in fluid communication with the interior of the rod housing 190 by means of the bore 210 through which the rod 182 and return spring 122 extend. It will be appreciated that the fluid communication may be by other or additional means. For example, one or more axial fluid passages may be provided in the structure or wall 212 surrounding the bore 210.

Figure 4:
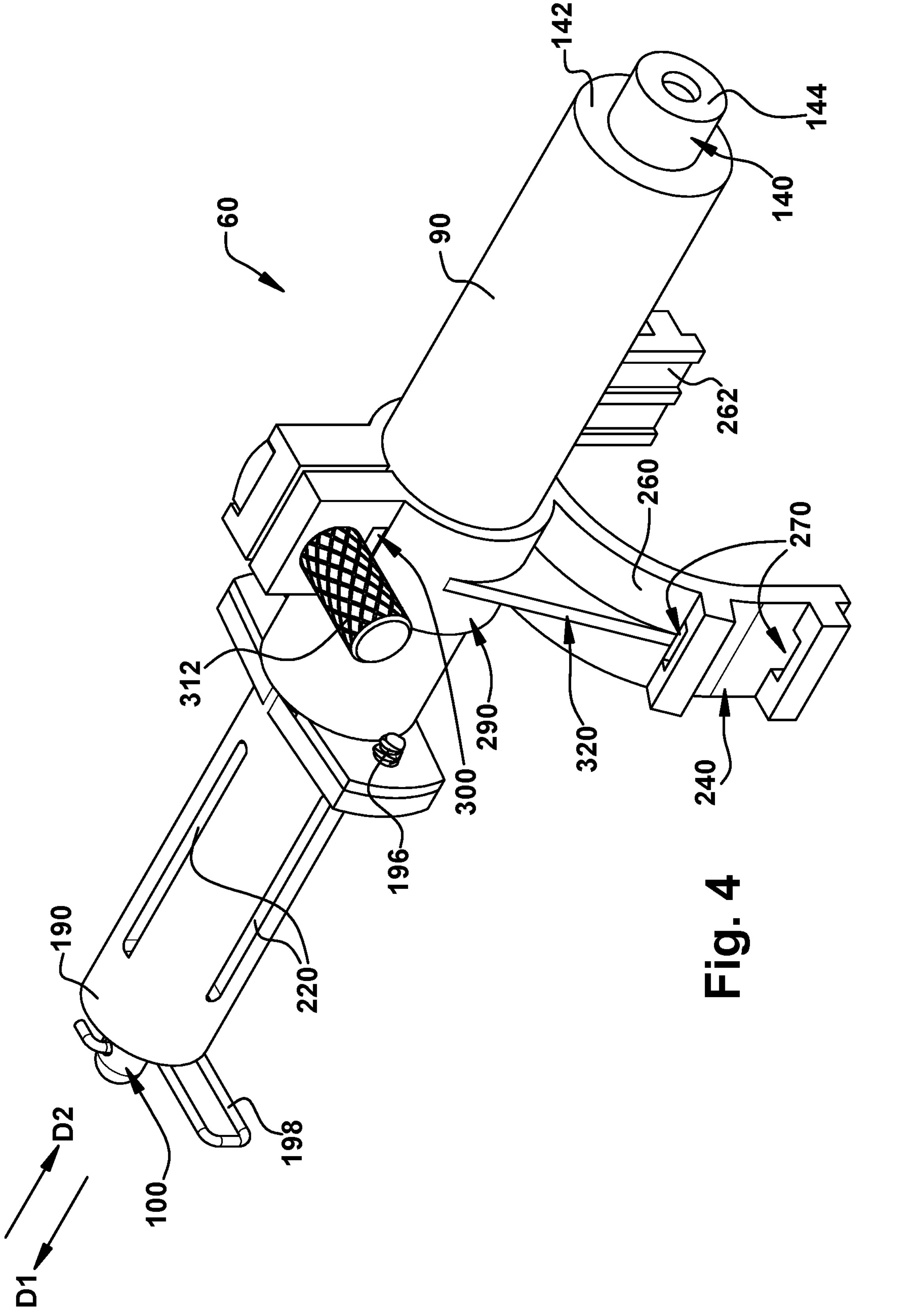
FIG. 4 is a perspective view of an actuation mechanism according to an embodiment of the invention.
Figure 7:
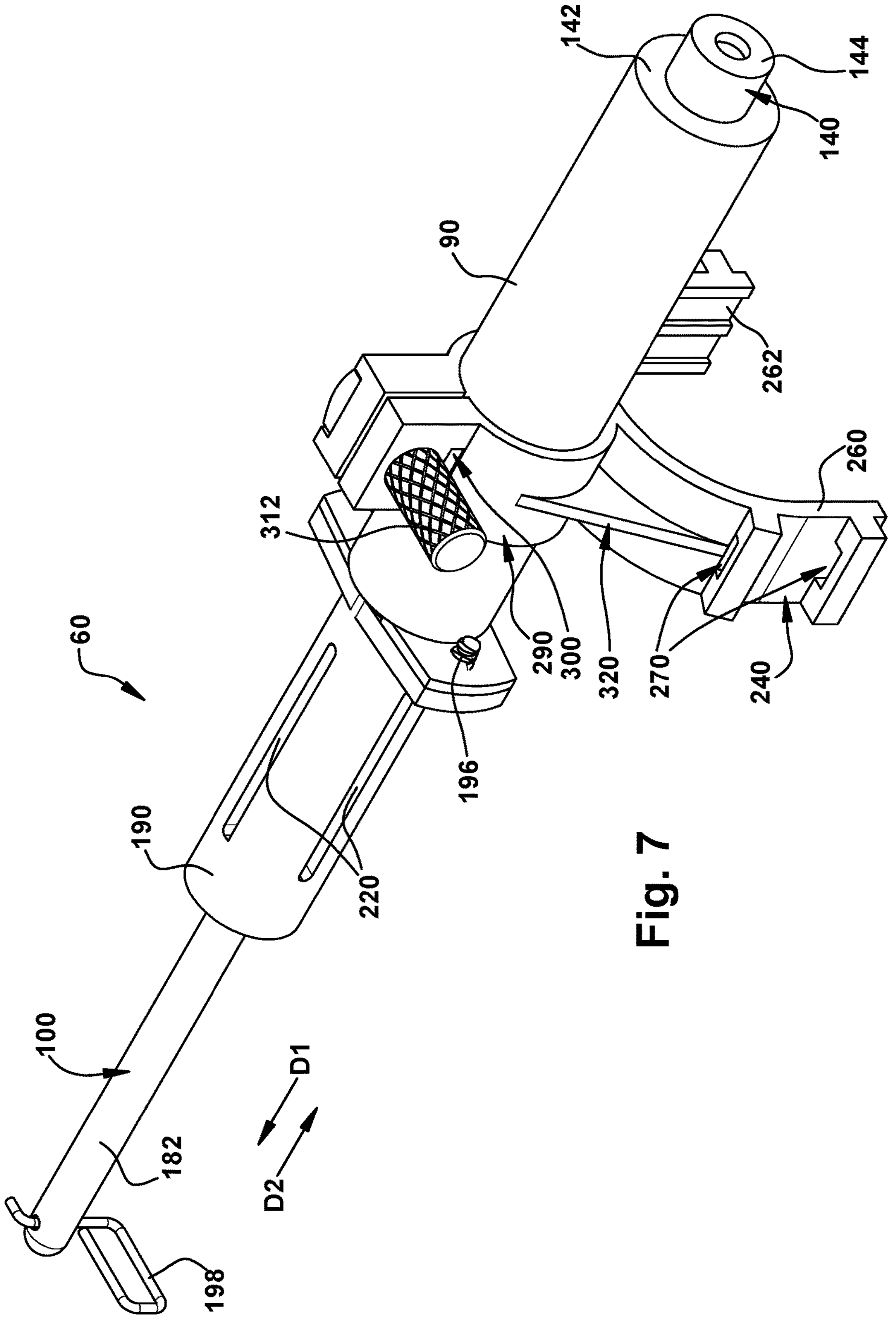
FIG. 7 is a perspective view of the FIG. 4 actuation mechanism, showing a plunger of the actuation mechanism in an extended position.

The rod housing 190 has at least one aperture 220 therein configured to enable cleaning solution to pass therethrough to the interior of the rod housing 190 and the rod side 174 of the piston cylinder 170. In the illustrated embodiment, four apertures 220 are angularly spaced 90 degrees apart about a central axis of the actuation mechanism 60, the central axis extending through the geometric center of the actuation mechanism 60, that is, in the direction of the first and second displacement directions D1, D2. The apertures 220 may be in the form of slots 220, that is, axially elongated and radially protruding openings. Advantageously, the slots 220 enable cleaning solution to enter the actuation mechanism 60 when submerged in the basin 70 during a cleaning cycle, enabling the actuation mechanism 60 to be cleaned during the cleaning cycle. In this way, when the cleaning cycle is complete the internal channels and the external surfaces of both the endoscope 20 and the actuation mechanism 60 are clean. Thus, for example, as the controller 130 of the reprocessor 10 executes a reprocessing cycle, the pump 64 may provide a pressure that will alternate between the first pressure and the second pressure, the first pressure being a pressure that is sufficient for the plunger 100 to overcome the spring biasing force of the return spring 122 and move to an extended position as shown in FIG. 7 and the second pressure being a pressure sufficient to enable the return spring 122 to return the plunger 100 to a retracted position as shown in FIGS. 4 and 6. The controller 130 is configured to actuate the plunger 100 over a range of motion achievable by the elevator guidewire lever 38 and associated elevator guidewire 30 and elevator 50 of the endoscope 20, which motion may be a single extension and retraction of the plunger 100 or a plurality of extensions and retractions, that is, reciprocating motion, to have the cleaning solution reach the elevator guidewire channel 34 of the endoscope 20 while simultaneously reaching the interior of the actuation mechanism 60 by means of the slots 220.

As noted above, the actuator housing 90 and endoscope 20 are in fixed positions relative to one another. In this way, when the pump 64 supplies the pressurized fluid to the receiving chamber 110 to actuate the plunger 100, the plunger 100 moves relative to the endoscope 20, and the actuator housing 90 remains fixed relative to the endoscope 20. A mounting saddle 240 may be used to fix the actuator housing 90 relative to the endoscope 20 which is described in more detail below. As noted above, the fixation of the actuator housing 90 and the endoscope 20 may also, or alternatively, be achieved by one or more straps or clamps that fix the actuator housing 90 and the endoscope 20 to one or more interior walls of the basin 70 of the endoscope reprocessor 10.

Referring now to FIGS. 4-9, the actuator housing 90 may be removably mountable to the endoscope 20. In the illustrated embodiment, a mounting saddle 240 is configured to mount the actuator housing 90 to the handle 40 of the endoscope 20. As shown in FIGS. 8 and 9, once the mounting saddle 240 mounts the actuator housing 90 to the handle 40, the actuation mechanism 60 is oriented such that the actuation of the plunger 100 displaces the elevator guidewire lever 38 to effect displacement of the elevator guidewire 30 within the elevator guidewire channel 34 of the endoscope 20. The mounting saddle 240 may be made of a flexible plastic so that the mounting saddle 240 can be placed over the handle 40 of the endoscope 20 and held in place, for example, by a zip tie. The flexibility enables the actuation mechanism 60 to be adjusted in a variety of positions along the endoscope 20 and thus capable of use with more than one size or type of endoscope 20.

In the illustrated embodiment, the mounting saddle 240 includes a first arm 260 and a second arm 262 that are configured to abut opposite sides of the handle 40. The first and second arms 260, 262 are each configured with a zip tie passage 270 to accommodate a zip tie 280. The zip tie 280 is configured to extend through the zip tie passage 270 of each arm 260, 262 and wrap around a portion of the actuator housing 90 and a portion of the handle 40 such that, when tightened, the zip tie 280 mounts the actuator housing 90 to the handle 40. The mounting saddle 240 may be positioned along the handle 40 in such a way that when the zip tie 280 is tightened the zip tie 280 is directly adjacent to a shoulder 284 of the endoscope 20. This aids in preventing the mounting saddle 240 and thus the actuation mechanism 60 from sliding along the length of the endoscope 20 when the actuation mechanism 60 actuates the plunger 100 to move the elevator guidewire lever 38 and the associated elevator guidewire 30 and elevator 50 of the endoscope during a reprocessing cycle.

The actuation mechanism 60 may also include a clamp 290 configured, when tightened, to secure the actuator housing 90 in a fixed position relative to the clamp 290. The clamp 290 may be provided with a zip tie passage 300 to accommodate a zip tie 310. The zip tie 310 may be configured to extend through the zip tie passage 300 and wrap around a portion of the actuator housing 90 and a portion of the handle 40 such that, when tightened, the zip tie 310 mounts the actuator housing 90 to the handle 40. As shown in FIGS. 8 and 9, once the clamp 290 mounts the actuator housing 90 to the handle 40, the actuation mechanism 60 is oriented such that the actuation of the plunger 100 displaces the elevator guidewire lever 38 to effect displacement of the elevator guidewire 30 within the elevator guidewire channel 34 of the endoscope 20. The clamp 290 may be configured to slidably receive the actuator housing 90 axially forwards and/or rearwards and configured, when tightened, to secure the actuation mechanism 60 in a fixed axial position relative to the clamp 290. In this way, the position of the piston cylinder 170 in the actuation mechanism 60 may be adjusted to fit any of a variety of endoscopes. The actuation mechanism 60 may include a thumb screw 312 for tightening the clamp 290 to the actuator housing 90.

In the illustrated embodiment, the zip tie 310 and the zip tie 280 form a single continuous zip tie 280, 310 that extends through the zip tie passages 270 of the first and second arms 260, 262 as well as the zip tie passage 300 of the clamp 290. In this regard, and as shown in FIGS. 4-9, the first and second arms 260, 262 and the clamp 290 may be connected together by an intermediate bridge 320 such that, when viewed in side elevation view, the first and second arms 260, 262 and the clamp 290 are aligned axially, as are their respective zip tie passages 270, 300, along the central axis of the actuation mechanism 60. In one form, the first and second arms 260, 262, the clamp 290, and the intermediate bridge 320 may be a single component made of a monolithic structure. The clamp 290, when tightened, secures the actuator housing 90 in a fixed position relative to the mounting saddle 240 and, accordingly, to the handle 40 of the endoscope 20. Other embodiments are contemplated. For example, the mounting saddle 240 and the clamp 290 may be discrete components axially spaced apart along the central axis of the actuation mechanism 60.

Figure 10:
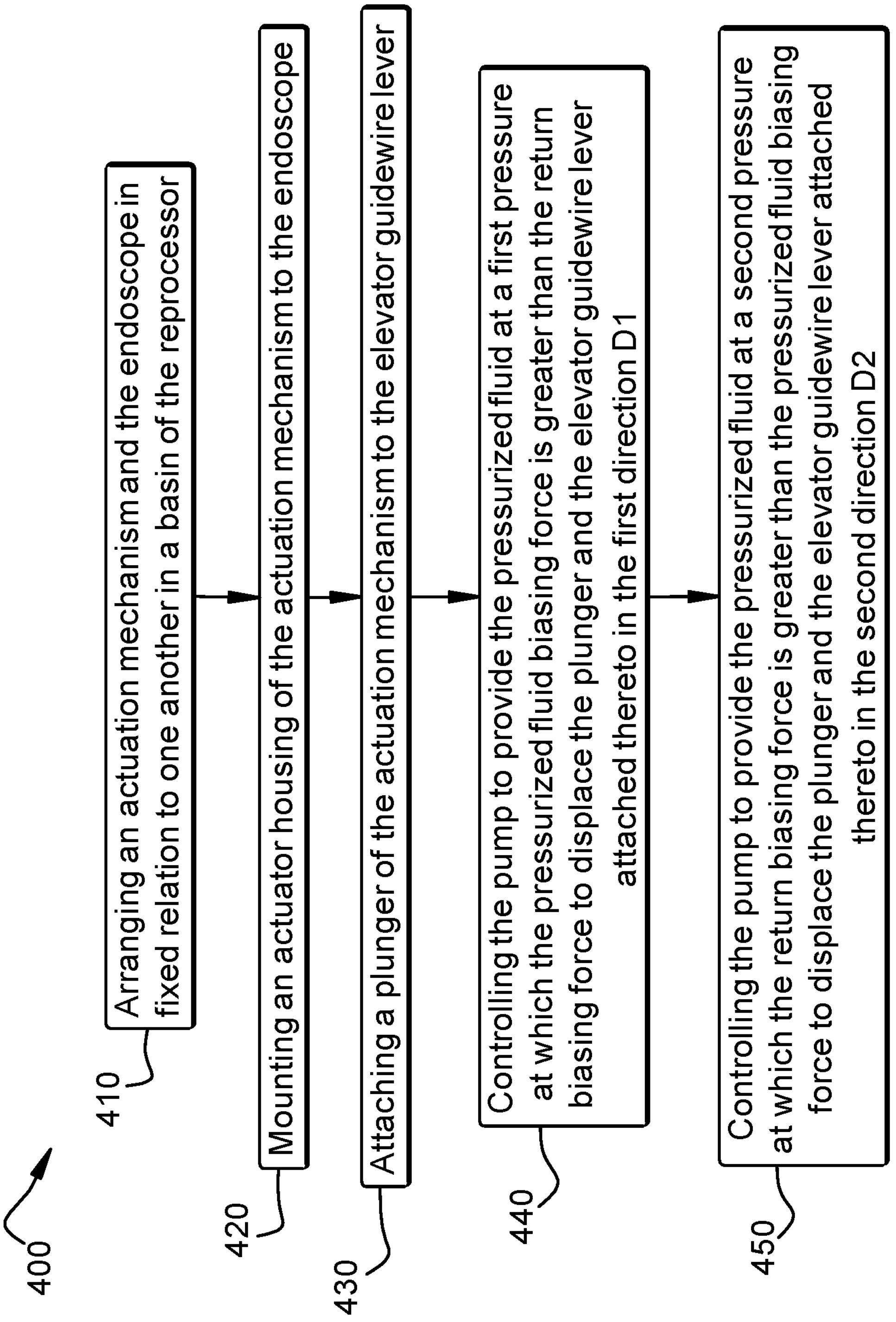
FIG. 10 shows a flowchart of a method in accordance with an embodiment of the invention.

Referring now to FIG. 10, a flowchart 400 for a method of reprocessing an endoscope 20 in an endoscope reprocessor, such as the reprocessor 10, is shown. The endoscope 20 may include an elevator guidewire 30 that passes through an elevator guidewire channel 34 of the endoscope 20 from an elevator guidewire lever 38 in a handle 40 at a first end 42 of the endoscope 20 to an elevator 50 in a second end 52 of the endoscope 20. Step 410 of the method may include arranging an actuation mechanism 60 and the endoscope 20 in fixed relation to one another in a basin 70 of the reprocessor 10. Step 420 may include mounting an actuator housing 90 of the actuation mechanism 60 to the endoscope 20. Step 430 may include attaching a plunger 100 of the actuation mechanism 60 to the elevator guidewire lever 38. The actuation mechanism 60 may include a receiving chamber 110 to receive pressurized fluid from a pump 64 of the reprocessor 10 to impart a pressurized fluid biasing force that displaces the plunger 100 relative to the actuator housing 90 in a first direction D1 and a return actuator 120 that imparts a biasing force that displaces the plunger 100 relative to the actuator housing 90 in a second direction D1 that is opposite to the first direction D1. Step 440 may include controlling the pump 64 to provide the pressurized fluid at a first pressure at which the pressurized fluid biasing force is greater than the return biasing force to displace the plunger 100 and the elevator guidewire lever 38 attached thereto in the first direction D1. Step 450 may include controlling the pump 64 to provide the pressurized fluid at a second pressure at which the return biasing force is greater than the pressurized fluid biasing force to displace the plunger 100 and the elevator guidewire lever 38 attached thereto in the second direction D2. The displacing of the plunger 100 and the elevator guidewire lever 38 attached thereto actuates the elevator guidewire 30 in the elevator guidewire channel 34 of the endoscope 20.

The return actuator 120 may include a return spring 122, and the return biasing force may include a spring biasing force, and controlling the pump 64 may include providing the pressurized fluid at the second pressure at which the spring biasing force is greater than the pressurized fluid biasing force to displace the plunger 100 and the elevator guidewire lever 38 attached thereto in the second direction D2.

The controlling step may include repeatedly displacing the plunger 100 and the elevator guidewire lever 38 attached thereto in the first and second directions D1, D2.

The inventor found that moving the elevator guidewire 30 while decontaminant solution is passing through the elevator guidewire channel 34 aids in more completely saturating the surfaces that would otherwise see reduced amounts of solution. The actuation mechanism 60 may be designed to actuate the elevator guidewire 30 autonomously by using the water pressure of the reprocessor 10 and the return actuator 120. The illustrated actuation mechanism 60 is made up of the plunger 100 including the piston 180 and rod 182, the return actuator 120 including the return spring 122, the piston cylinder 170, the rod housing 190, the lever loop 198, the mounting saddle 240, and the clamp 290. The elevator guidewire lever 38 is connected to the piston 180 using the lever loop 198 that fits over the elevator guidewire lever 38. Water and/or decontaminant solution is supplied to the piston cylinder 170 through the conduit 160 connected by the quick turn fitting 144. Supplying fluid pressure to the piston cylinder 170 urges the piston 180 forward in the first direction D1, causing the return spring 122 of the return actuator 120 to compress, pushing the elevator guidewire lever 38 to, for example, a first limit position. Shutting the water and/or decontaminant solution off and reducing or eliminating the fluid pressure enables the return spring 122 to unflex, i.e., expand, thereby retracting the piston 180 in the second direction D2, and pulling the elevator guidewire lever 38 back to, for example, a second limit position. The first and second limit positions may be the most-forward and most-rearward limit positions of the elevator guidewire lever 38, or other positions to realize movement of the elevator guidewire 30 to aid in cleaning the elevator guidewire channel 34. This process can be repeated as many times as desired or necessary to clean or decontaminate the elevator guidewire channel 34.

The mounting saddle 240 is made of a flexible plastic so it can be placed over the handle 40 of the endoscope 20 and held in place by the zip tie 280 without interfering with the structure or components of the endoscope 20. In the illustrated embodiment, the mounting saddle 240 is also where the piston 180 is mounted. The actuation mechanism 60 also includes the clamp 290, which in the illustrated embodiment is connected to the mounting saddle 240. The clamp 290, among other things, enables the piston cylinder 170 to be moved forwards and/or backwards. A thumb screw 312 may be tightened to fix the piston cylinder 170 in a single location. As such, the position of the piston cylinder 170 in the mounting saddle 240 can be adjusted to accommodate a variety of endoscopes.

The rod housing 190 is fixed to the end of the piston cylinder 170. The rod housing 190 may include a cap for containing the return spring 122 in the piston cylinder 170. Apertures 220 in the form of slots 220 in the rod housing 190 enable cleaning solution to enter the actuation mechanism 60 when submerged enabling the actuation mechanism 60 to be cleaned during the cleaning cycle. The plunger 100 has the piston 180 on one end to enable positive pressure to be built up in the piston side 172 of the piston cylinder 170. This positive pressure moves the piston 180 and thus the plunger 100 of which it is a part in the first direction D1. The plunger 100 also has the rod 182 that extends just beyond the end wall 192 of the rod housing 190, which is where the lever loop 198 is attached. The return spring 122 fits over the rod 182, which aids the return spring 122 in compressing without buckling.

The connection port 140 on the piston cylinder 170 connects to the flexible conduit 160 which in turn connects the actuation mechanism 60 to the plumbing of the reprocessor 10. The connection port 140 may include the quick turn fitting 144. The connection port 140 enables the receiving chamber 110 of the piston cylinder 170 to receive pressurized fluid. The available fluid pressure and the spring constant of the return spring 122 are two factors in determining the inner diameter of the piston cylinder 170, which supplies the mechanical force needed to actuate the elevator guidewire lever 38. The inner diameter of the piston cylinder 170 enables the fluid pressure to compress the return spring 122 to push the elevator guidewire lever 38 to its limit position. The return spring 122 of the return actuator 120 may be used to evacuate the cleaning solution or water in the piston cylinder 170. As the compressed return spring 122 unflexes, i.e., extends, the return spring 122 also pulls the elevator guidewire lever 38 to its original or retracted position.

Several advantages are realized by the actuation mechanism 60. The actuation mechanism 60 includes an automated means to actuate the elevator guidewire 30 using fluid pressure, while the endoscope 20 is being cleaned by the reprocessor 10. Using the cleaning fluid with the working pressure of the fluid, self-cleans the actuation mechanism 60 while also eliminating the need to manually rotate the elevator guidewire lever 38. The use of the plunger 100 makes for a more efficient cleaning of the elevator guidewire channel 34, reducing the amount of travel the elevator guidewire lever 38 sees. The actuation mechanism 60 uses merely water pressure and the return actuator 120, which may include for example the return spring 122, to actuate the elevator guidewire lever 38 in two opposite directions D1, D2 to achieve better cleaning results of the elevator guidewire channel 34 and the distal tip of the endoscope 20.

As noted earlier, in an alternate embodiment, the piston cylinder 170 can be changed by adding another fluid pressure connection port to the opposite end of piston cylinder 170, to realize a double acting piston-cylinder. Of course, even such a double acting piston-cylinder configuration may employ the return spring 122, for example, to aid in retracting the rod 182. This alternate double-acting piston cylinder arrangement may include an exhaust valve to divert the fluid pressure from the piston side 172 of the piston 180 to the rod side 174 of the piston 180, and vice versa to control displacement of the piston 180 in the first and second directions D1, D2. In another embodiment, air may be used to actuate the piston 180 instead of water and/or cleaning solution.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An endoscope reprocessor for reprocessing an endoscope having an elevator guidewire that passes through an elevator guidewire channel of the endoscope from an elevator guidewire lever in a handle at a first end of the endoscope to an elevator in a second end of the endoscope, the reprocessor comprising:

an actuation mechanism;

a basin in which the actuation mechanism and the endoscope may be arranged in fixed relation to one another;

a pump that provides pressurized fluid;

wherein the actuation mechanism includes an actuator housing and a plunger removably attachable to the elevator guidewire lever, wherein the actuation mechanism includes a receiving chamber to receive the pressurized fluid from the pump to impart a pressurized fluid biasing force that displaces the plunger relative to the actuator housing in a first direction and a return actuator that imparts a return biasing force that displaces the plunger relative to the actuator housing in second direction that is opposite to the first direction; and, a controller to control the pump to provide the pressurized fluid at a first pressure such that the pressurized fluid biasing force in the receiving chamber is greater than the return biasing force of the return actuator to displace the plunger and the elevator guidewire lever attached thereto in the first direction and a second pressure at such that the pressurized fluid biasing force in the receiving chamber is lesser than the return biasing force of the return actuator to displace the plunger and the elevator guidewire lever attached thereto in the second direction opposite the first direction, wherein the displacing of the plunger and the elevator guidewire lever attached thereto actuates the elevator guidewire in the elevator guidewire channel of the endoscope.

2. The endoscope reprocessor of claim 1, wherein the return actuator includes a return spring, and the return biasing force includes a spring biasing force.

3. The endoscope reprocessor of claim 1, wherein the actuation mechanism includes a connection port to connect the receiving chamber to a conduit of the pump to receive the pressurized fluid from the pump.

4. The endoscope reprocessor of claim 3, further comprising a quick turn fitting to connect the conduit to the connection port of the actuation mechanism.

5. The endoscope reprocessor of claim 1, wherein the actuator housing includes a piston cylinder, and the plunger includes a piston and a rod extending axially from the piston, wherein the piston cylinder slidably axially receives the piston therein.

6. The endoscope reprocessor of claim 5, wherein the piston cylinder has a piston side on one side of the piston and a rod side on the opposite side of the piston, the rod side being the side where the rod extends from the piston, and wherein the piston side forms the receiving chamber of the actuation mechanism.

7. The endoscope reprocessor of claim 5, wherein the actuation mechanism includes a rod housing fixed axially to an end of the piston cylinder, and wherein the rod extends axially from the piston to beyond an end wall of the rod housing through an opening in the end wall.

8. The endoscope reprocessor of claim 7, wherein a portion of the rod extending beyond the end wall of the rod housing includes a lever loop attached thereto, wherein the lever loop is removably attachable to the elevator guidewire lever.

9. The endoscope reprocessor of claim 7, wherein the return spring comprises a compression spring that circumscribes the rod and includes one end constrained by the piston and an opposite end constrained by the end wall of the rod housing.

10. The endoscope reprocessor of claim 9, wherein the compression spring is configured to be compressed at least partially in the rod housing as the plunger is displaced in the first direction.

11. The endoscope reprocessor of claim 10, wherein the rod housing has at least one aperture therein configured to enable cleaning solution to pass therethrough to the interior of the rod housing and the rod side of the piston cylinder.

12. The endoscope reprocessor of claim 7, wherein the piston cylinder has a piston side on one side of the piston and a rod side on the opposite side of the piston, the rod side being the side where the rod extends from the piston, and wherein the rod side is in fluid communication with the interior of the rod housing.

13. The endoscope reprocessor of claim 1, wherein the actuator housing is removably mountable to the endoscope.

14. The endoscope reprocessor of claim 1, wherein the actuation mechanism includes a mounting saddle configured to mount the actuator housing to the handle of the endoscope.

15. The endoscope reprocessor of claim 14, wherein the mounting saddle is made of a flexible plastic.

16. The endoscope reprocessor of claim 14, wherein the mounting saddle includes first and second arms that are configured to abut opposite sides of the handle, each of the first and second arms being configured with a zip tie passage to accommodate a zip tie, wherein the actuation mechanism includes a zip tie configured to extend through the zip tie passages and wrap around a portion of the actuator housing and a portion of the handle such that, when tightened, the zip tie mounts the actuator housing to the handle.

17. The endoscope reprocessor of claim 1, wherein the actuation mechanism includes a clamp configured, when tightened, to secure the actuator housing in a fixed position relative to the clamp, the clamp being configured with a zip tie passage to accommodate a zip tie, wherein the actuation mechanism includes a zip tie configured to extend through the zip tie passage and wrap around a portion of the actuator housing and a portion of the handle such that, when tightened, the zip tie mounts the actuator housing to the handle.

18. The endoscope reprocessor of claim 17, wherein the actuation mechanism includes a thumb screw for tightening the clamp to the actuator housing.

19. The endoscope reprocessor of claim 17, wherein the actuation mechanism includes a mounting saddle configured to mount the actuator housing to the handle of the endoscope, and wherein the clamp and the mounting saddle are connected together and the clamp, when tightened, secures the actuator housing in a fixed position relative to the mounting saddle.

20. The endoscope reprocessor of claim 1, wherein the clamp is configured to slidably receive the actuator housing axially forwards and/or rearwards and configured, when tightened, to secure the actuator housing in a fixed axial position relative to the clamp.

21. The endoscope reprocessor of claim 1, wherein the actuation mechanism is sized to be removably insertable in the basin, and the reprocessor comprises a lid configured to seal the basin with the actuation mechanism and endoscope therein from the exterior of the reprocessor.

22. A method of reprocessing an endoscope having an elevator guidewire that passes through an elevator guidewire channel of the endoscope from an elevator guidewire lever in a handle at a first end of the endoscope to an elevator in a second end of the endoscope, the method comprising:

arranging an actuation mechanism and the endoscope in fixed relation to one another in a basin of the reprocessor;

mounting an actuator housing of the actuation mechanism to the endoscope and attaching a plunger of the actuation mechanism to the elevator guidewire lever, wherein the actuation mechanism includes a receiving chamber to receive pressurized fluid from a pump of the reprocessor to impart a pressurized fluid biasing force that displaces the plunger relative to the actuator housing in a first direction and a return actuator that imparts a return biasing force that displaces the plunger relative to the actuator housing in a second direction that is opposite to the first direction; and controlling the pump to provide the pressurized fluid at a first pressure such that the pressurized fluid biasing force in the receiving chamber is greater than the return biasing force of the return actuator to displace the plunger and the elevator guidewire lever attached thereto in the first direction and a second pressure such that the pressurized fluid biasing force in the receiving chamber is lesser than the return biasing force of the return actuator to displace the plunger and the elevator guidewire lever attached thereto in the second direction opposite the first direction, wherein the displacing of the plunger and the elevator guidewire lever attached thereto actuates the elevator guidewire in the elevator guidewire channel of the endoscope.

23. The method of claim 22, wherein the return actuator includes a return spring, and the return biasing force includes a spring biasing force, and controlling the pump to provide the pressurized fluid at the second pressure at which the spring biasing force is greater than the pressurized fluid biasing force to displace the plunger and the elevator guidewire lever attached thereto in the second direction.

24. The method of claim 22, wherein controlling the pump includes repeatedly displacing the plunger and the elevator guidewire lever attached thereto in the first and second directions.

25. An endoscope reprocessor for reprocessing an endoscope having an elevator guidewire that passes through an elevator guidewire channel of the endoscope from an elevator guidewire lever in a handle at a first end of the endoscope to an elevator in a second end of the endoscope, the reprocessor comprising:

an actuation mechanism;

a basin in which the actuation mechanism and the endoscope may be arranged in fixed relation to one another;

a pump that provides pressurized fluid;

wherein the actuation mechanism includes an actuator housing and a plunger removably attachable to the elevator guidewire lever, wherein the actuation mechanism includes a receiving chamber to receive the pressurized fluid from the pump to impart a pressurized fluid biasing force that displaces the plunger relative to the actuator housing in a first direction and a return actuator that imparts a return biasing force that displaces the plunger relative to the actuator housing in second direction that is opposite to the first direction; and, a controller to control the pump to provide the pressurized fluid at a first pressure at which the pressurized fluid biasing force is greater than the return biasing force to displace the plunger and the elevator guidewire lever attached thereto in the first direction and a second pressure at which the return biasing force is greater than the pressurized fluid biasing force to displace the plunger and the elevator guidewire lever attached thereto in the second direction, wherein the displacing of the plunger and the elevator guidewire lever attached thereto actuates the elevator guidewire in the elevator guidewire channel of the endoscope, wherein the actuation mechanism includes a rod housing attached to the actuator housing, wherein the rod housing includes at least one aperture therein on a side of the plunger adjacent the return actuator and the at least one aperture is configured to enable cleaning solution to pass therethrough to an interior of the rod housing.

* * * * *